(12) United States Patent
Bluth

(10) Patent No.: US 9,743,844 B2
(45) Date of Patent: Aug. 29, 2017

(54) COMMUNITY BASED MANAGED HEALTH KIOSK AND PRESCRIPTION DISPENSEMENT SYSTEM

(75) Inventor: Charles P. Bluth, Glenbrook, NV (US)

(73) Assignee: COMPUTERIZED SCREENING, INC., Reno, NV (US)

( * ) Notice: Subject to any disclaimer, the term of this patent is extended or adjusted under 35 U.S.C. 154(b) by 1372 days.

(21) Appl. No.: 12/407,657

(22) Filed: Mar. 19, 2009

(65) Prior Publication Data

US 2009/0240528 A1 Sep. 24, 2009

Related U.S. Application Data

(60) Provisional application No. 61/070,309, filed on Mar. 21, 2008.

(51) Int. Cl.
| | | |
|---|---|---|
| *G06Q 50/00* | (2012.01) | |
| *A61B 5/0205* | (2006.01) | |
| *A61B 5/00* | (2006.01) | |
| *G06Q 40/00* | (2012.01) | |
| *G06Q 50/22* | (2012.01) | |
| *G06Q 50/24* | (2012.01) | |
| *G06F 19/00* | (2011.01) | |
| *A61B 5/022* | (2006.01) | |
| *A61B 5/1172* | (2016.01) | |
| *A61B 5/145* | (2006.01) | |

(52) U.S. Cl.
CPC ...... *A61B 5/02055* (2013.01); *A61B 5/14546* (2013.01); *A61B 5/6888* (2013.01); *A61B 5/702* (2013.01); *G06F 19/323* (2013.01); *G06F 19/328* (2013.01); *G06F 19/3418* (2013.01); *G06F 19/3462* (2013.01); *G06F 19/363* (2013.01); *G06Q 40/00* (2013.01); *G06Q 50/22* (2013.01); *G06Q 50/24* (2013.01); *A61B 5/0013* (2013.01); *A61B 5/022* (2013.01); *A61B 5/1172* (2013.01); *A61B 5/145* (2013.01); *A61B 5/14532* (2013.01); *A61B 5/743* (2013.01)

(58) Field of Classification Search
CPC ............................... G06Q 50/22; G06Q 50/24
USPC .......................................................... 705/2, 3
See application file for complete search history.

(56) References Cited

U.S. PATENT DOCUMENTS

| 3,935,984 A | 2/1976 | Lichowsky et al. |
| 4,013,135 A | 3/1977 | Kechely |

(Continued)

FOREIGN PATENT DOCUMENTS

| EP | 219395 | 4/1987 |
| EP | 0329306 A1 | 8/1989 |

(Continued)

OTHER PUBLICATIONS

Holdfelder, A Networked Multimedia Retrieval Management System for Distributed Kiosk Applications, 1994 (IEEE).

(Continued)

*Primary Examiner* — Lena Najarian
(74) *Attorney, Agent, or Firm* — Baker & Hostetler LLP

(57) ABSTRACT

The present invention is directed to systems and methods that provide community based managed health kiosks and prescription drug dispensing systems, and more particularly to facilitating automated drug dispensement by a kiosk system following authorization by a remotely located health care professional who can monitor and communicate with a patient via the kiosk system.

6 Claims, 5 Drawing Sheets

(56) References Cited

U.S. PATENT DOCUMENTS

| | | |
|---|---|---|
| 4,109,646 A | 8/1978 | Keller |
| D250,896 S | 1/1979 | Huber et al. |
| D254,629 S | 4/1980 | Yen |
| 4,206,765 A | 6/1980 | Huber |
| D259,509 S | 6/1981 | Loeffler et al. |
| 4,274,424 A | 6/1981 | Kimura et al. |
| D262,139 S | 12/1981 | Duckat |
| 4,582,151 A | 4/1986 | Mairot et al. |
| D290,876 S | 7/1987 | Arduin et al. |
| 4,677,983 A | 7/1987 | Yamaguchi et al. |
| 4,731,726 A | 3/1988 | Allen, III |
| D297,364 S | 8/1988 | Slater |
| 4,776,339 A | 10/1988 | Schreiber |
| 4,780,599 A | 10/1988 | Baus |
| 4,799,562 A | 1/1989 | Burrows et al. |
| 4,803,625 A | 2/1989 | Fu et al. |
| 4,962,550 A | 10/1990 | Ikenaga et al. |
| 4,998,534 A | 3/1991 | Claxton, III et al. |
| 5,054,495 A | 10/1991 | Uemura et al. |
| 5,075,850 A * | 12/1991 | Asahioka et al. ............... 704/2 |
| 5,118,062 A | 6/1992 | Archambault |
| 5,140,991 A | 8/1992 | Niwa |
| 5,177,912 A | 1/1993 | Ball |
| 5,217,181 A | 6/1993 | Hammarskjold et al. |
| 5,278,753 A * | 1/1994 | Graft, III ..................... 705/12 |
| 5,291,399 A | 3/1994 | Chaco |
| 5,292,177 A | 3/1994 | Balderi et al. |
| 5,307,263 A | 4/1994 | Brown |
| 5,351,186 A | 9/1994 | Bullock |
| 5,361,871 A | 11/1994 | Gupta et al. |
| 5,380,269 A | 1/1995 | Urso |
| 5,410,471 A | 4/1995 | Alyfuku et al. |
| 5,441,047 A | 8/1995 | David et al. |
| D371,844 S | 7/1996 | Sadritabrizi et al. |
| 5,533,511 A | 7/1996 | Kaspari et al. |
| 5,537,289 A | 7/1996 | Dahl |
| 5,542,420 A | 8/1996 | Goldman et al. |
| 5,547,270 A | 8/1996 | Dang |
| 5,549,117 A | 8/1996 | Tacklind et al. |
| 5,558,638 A | 9/1996 | Evers et al. |
| 5,595,180 A | 1/1997 | Ogura et al. |
| 5,626,144 A | 5/1997 | Tacklind et al. |
| 5,634,468 A | 6/1997 | Platt et al. |
| 5,647,369 A | 7/1997 | Petrucelli et al. |
| 5,678,562 A | 10/1997 | Sellers |
| 5,704,362 A | 1/1998 | Hersh et al. |
| 5,704,366 A | 1/1998 | Tacklind et al. |
| 5,710,551 A | 1/1998 | Ridgeway |
| 5,713,856 A | 2/1998 | Eggers |
| 5,727,560 A | 3/1998 | Ogura |
| 5,765,910 A | 6/1998 | Larkin et al. |
| 5,781,909 A | 7/1998 | Logan et al. |
| 5,801,755 A | 9/1998 | Echerer |
| 5,826,267 A | 10/1998 | McMillan |
| 5,833,602 A | 11/1998 | Osemwota |
| 5,853,371 A | 12/1998 | Inukai et al. |
| 5,857,967 A | 1/1999 | Frid et al. |
| 5,867,821 A | 2/1999 | Ballantyne et al. |
| 5,890,128 A | 3/1999 | Diaz |
| 5,897,493 A | 4/1999 | Brown |
| 5,899,855 A | 5/1999 | Brown |
| 5,899,980 A | 5/1999 | Wilf et al. |
| 5,899,998 A | 5/1999 | McGauley et al. |
| 5,913,210 A | 6/1999 | Call |
| 5,918,696 A | 7/1999 | Van Voorhies |
| 5,951,300 A | 9/1999 | Brown |
| 5,954,640 A | 9/1999 | Szabo |
| 5,959,529 A | 9/1999 | Kail, IV |
| 5,961,451 A | 10/1999 | Reber et al. |
| 5,967,600 A | 10/1999 | Jelacic et al. |
| 5,970,474 A | 10/1999 | LeRoy et al. |
| 5,974,124 A | 10/1999 | Schlueter et al. |
| 5,978,777 A | 11/1999 | Garnier |
| 5,987,352 A | 11/1999 | Klein et al. |
| 5,987,519 A | 11/1999 | Peifer et al. |
| 5,997,476 A | 12/1999 | Brown |
| 6,024,281 A | 2/2000 | Shepley |
| 6,024,699 A | 2/2000 | Surwit et al. |
| 6,029,141 A | 2/2000 | Bezos et al. |
| 6,032,119 A | 2/2000 | Brown |
| 6,045,510 A | 4/2000 | Ogura et al. |
| 6,046,761 A | 4/2000 | Echerer |
| 6,050,924 A | 4/2000 | Shea |
| 6,050,940 A | 4/2000 | Braun et al. |
| 6,080,106 A | 6/2000 | Lloyd et al. |
| 6,085,195 A * | 7/2000 | Hoyt et al. |
| 6,101,478 A | 8/2000 | Brown |
| 6,102,856 A | 8/2000 | Groff et al. |
| 6,110,108 A | 8/2000 | Shimura et al. |
| 6,122,351 A | 9/2000 | Schlueter, Jr. et al. |
| 6,144,837 A | 11/2000 | Quy |
| 6,148,297 A | 11/2000 | Swor et al. |
| 6,154,738 A | 11/2000 | Call |
| 6,155,179 A | 12/2000 | Aust et al. |
| 6,168,563 B1 | 1/2001 | Brown |
| 6,176,826 B1 | 1/2001 | Shimura et al. |
| 6,190,313 B1 | 2/2001 | Hinkle |
| 6,206,829 B1 | 3/2001 | Iliff |
| 6,213,394 B1 | 4/2001 | Schumacher et al. |
| 6,213,953 B1 | 4/2001 | Reeves |
| 6,219,587 B1 | 4/2001 | Ahlin et al. |
| 6,221,012 B1 | 4/2001 | Maschke et al. |
| 6,225,901 B1 | 5/2001 | Kail, IV |
| 6,260,021 B1 | 7/2001 | Wong |
| 6,263,330 B1 | 7/2001 | Bessette |
| 6,283,761 B1 | 9/2001 | Joao |
| 6,286,029 B1 | 9/2001 | Delph |
| 6,289,115 B1 | 9/2001 | Takeo |
| 6,290,646 B1 | 9/2001 | Cosentino et al. |
| 6,308,283 B1 | 10/2001 | Galipeau et al. |
| 6,330,491 B1 | 12/2001 | Lion |
| 6,336,044 B1 | 1/2002 | Ghiassi et al. |
| 6,336,136 B1 | 1/2002 | Harris |
| 6,336,900 B1 | 1/2002 | Alleckson et al. |
| 6,364,834 B1 | 4/2002 | Reuss et al. |
| 6,379,301 B1 | 4/2002 | Worthington et al. |
| 6,381,029 B1 | 4/2002 | Tipirneni |
| 6,381,577 B1 | 4/2002 | Brown |
| 6,402,691 B1 | 6/2002 | Peddicord et al. |
| 6,403,897 B1 | 6/2002 | Bluth et al. |
| 6,416,471 B1 | 7/2002 | Kumar et al. |
| 6,418,441 B1 | 7/2002 | Call |
| 6,427,164 B1 | 7/2002 | Reilly |
| 6,428,124 B1 | 8/2002 | Bluth et al. |
| 6,440,068 B1 | 8/2002 | Brown et al. |
| 6,454,705 B1 | 9/2002 | Cosentino et al. |
| 6,454,708 B1 | 9/2002 | Ferguson et al. |
| 6,471,657 B2 | 10/2002 | Sadritabrizi |
| 6,473,740 B2 | 10/2002 | Cockrill et al. |
| 6,484,144 B2 | 11/2002 | Martin et al. |
| 6,484,939 B1 | 11/2002 | Blaeuer |
| 6,485,415 B1 | 11/2002 | Uchiyama et al. |
| 6,496,855 B1 | 12/2002 | Hunt et al. |
| 6,511,435 B1 | 1/2003 | Bluth et al. |
| 6,519,491 B2 | 2/2003 | Ishikawa |
| 6,525,670 B1 | 2/2003 | Doi et al. |
| 6,576,471 B2 | 6/2003 | Otvos |
| 6,581,038 B1 | 6/2003 | Mahran |
| 6,584,564 B2 | 6/2003 | Olkin et al. |
| 6,594,607 B2 | 7/2003 | Lavery |
| 6,595,929 B2 | 7/2003 | Stivoric et al. |
| 6,602,469 B1 | 8/2003 | Maus |
| 6,605,038 B1 | 8/2003 | Teller et al. |
| 6,606,606 B2 | 8/2003 | Starr |
| 6,609,106 B1 | 8/2003 | Robertson |
| 6,612,984 B1 | 9/2003 | Kerr, II |
| 6,638,218 B2 | 10/2003 | Bulat |
| 6,692,436 B1 | 2/2004 | Bluth |
| 6,699,195 B2 | 3/2004 | Nakazawa et al. |
| 6,705,990 B1 | 3/2004 | Gallant et al. |
| 6,752,760 B2 | 6/2004 | Kouou |
| 6,790,178 B1 | 9/2004 | Mault et al. |
| 6,826,572 B2 | 11/2004 | Colace et al. |
| 6,912,507 B1 | 6/2005 | Phillips et al. |

(56) References Cited

U.S. PATENT DOCUMENTS

| | | |
|---|---|---|
| 7,246,069 B1 | 7/2007 | O'Hanlon et al. |
| 7,287,031 B1 | 10/2007 | Karpf et al. |
| 7,305,347 B1 | 12/2007 | Joao |
| 7,706,915 B2 | 4/2010 | Mohapatra et al. |
| 2001/0030546 A1 | 10/2001 | Yamada et al. |
| 2001/0034631 A1 | 10/2001 | Kiselik |
| 2001/0049470 A1 | 12/2001 | Mault et al. |
| 2001/0051881 A1 | 12/2001 | Filler |
| 2001/0056226 A1 | 12/2001 | Zodnik et al. |
| 2002/0010596 A1 | 1/2002 | Matory |
| 2002/0032501 A1 | 3/2002 | Tilles et al. |
| 2002/0046278 A1 | 4/2002 | Hays et al. |
| 2002/0082962 A1 | 6/2002 | Farris et al. |
| 2002/0087054 A1 | 7/2002 | Lin et al. |
| 2002/0090087 A1 | 7/2002 | Tamura et al. |
| 2002/0115912 A1 | 8/2002 | Muraki et al. |
| 2002/0120199 A1 | 8/2002 | Ogura et al. |
| 2002/0187248 A1* | 12/2002 | Childers .................. 427/2.1 |
| 2003/0046109 A1 | 3/2003 | Uchikubo |
| 2003/0061271 A1 | 3/2003 | Pittarelli |
| 2003/0078809 A1 | 4/2003 | LaCour |
| 2003/0125017 A1 | 7/2003 | Green et al. |
| 2003/0182161 A1 | 9/2003 | Vanderlei et al. |
| 2003/0190023 A1 | 10/2003 | Farkas et al. |
| 2004/0044560 A1 | 3/2004 | Giglio et al. |
| 2004/0077955 A1 | 4/2004 | Kawanishi et al. |
| 2004/0078216 A1 | 4/2004 | Toto |
| 2004/0078229 A1 | 4/2004 | Gay et al. |
| 2004/0093238 A1 | 5/2004 | Deakter |
| 2004/0116785 A1 | 6/2004 | Bulat |
| 2004/0138924 A1 | 7/2004 | Pristine |
| 2004/0162466 A1 | 8/2004 | Quy |
| 2004/0162740 A1* | 8/2004 | Ericsson et al. ............ 705/3 |
| 2004/0171460 A1 | 9/2004 | Park |
| 2004/0171955 A1 | 9/2004 | Morganroth |
| 2004/0204954 A1* | 10/2004 | Lacko ..................... 705/1 |
| 2004/0210457 A1 | 10/2004 | Sameh |
| 2005/0038326 A1 | 2/2005 | Mathur |
| 2005/0049746 A1* | 3/2005 | Rosenblum ............... 700/232 |
| 2005/0192841 A1 | 9/2005 | Hays et al. |
| 2006/0106646 A1* | 5/2006 | Squilla et al. ............. 705/3 |
| 2006/0193004 A1 | 8/2006 | Wasilewski et al. |
| 2007/0016618 A1 | 1/2007 | Robert et al. |
| 2007/0136096 A1 | 6/2007 | Okalebo et al. |
| 2007/0164103 A1 | 7/2007 | Berkowitz et al. |
| 2007/0226008 A1 | 9/2007 | Halsted et al. |
| 2007/0239549 A1 | 10/2007 | LaFauci et al. |
| 2007/0265869 A1* | 11/2007 | Ryckman et al. ............. 705/1 |
| 2008/0014867 A1 | 1/2008 | Finn |
| 2008/0081955 A1 | 4/2008 | Eisenhandler et al. |
| 2008/0114213 A1 | 5/2008 | Bagan |

FOREIGN PATENT DOCUMENTS

| | | |
|---|---|---|
| EP | 0422512 A1 | 4/1991 |
| FR | 2613918 | 4/1987 |
| FR | 19870005369 A1 | 11/1990 |
| WO | 9518564 A1 | 7/1995 |
| WO | PCT/US01/12082 | 1/2002 |

OTHER PUBLICATIONS

CardioAnalysis Systems, Owner's Manual Assembly Instructions, Apr. 1992.
U.S. Appl. No. 60/107,707, filed Nov. 2, 1998, Connolly et al.
U.S. Appl. No. 60/144,705, filed Jul. 20, 1999, Maus et al.
U.S. Appl. No. 09/619,077, filed Jul. 17, 2000, Hays, et al.
U.S. Appl. No. 09/654,146, filed Sep. 1, 2000, Hays.
U.S. Appl. No. 09/654,152, filed Sep. 1, 2000, Hays, et al.
U.S. Appl. No. 09/654,203, filed Sep. 1, 2000, Hays, et al.
Editors et al., "Lifeclinic announces rollout of web-enabled blood pressure kiosks to Kmart stores across the country", Nov. 2000, 3 pages.
LC600 Hardware Information, Lifeclinic, 2009, 1 page.
Nara, "Performance review of a noninvasive blood pressure monitor", Medical Electronics, Feb. 1996, 5 pages.
Sample Pharmacy, screenshot, Lifeclinic, 2009, 1 page.
Spacelabs Medical, Spacelabs expands telemedicine solution with access to comprehensive patient records, Feb. 1999, 2 pages.
Spacelabs Medical, Vita-stat health screening products, Feb. 1996, 2 pages.
Vaczek, "Phar-more tests blood pressure with new POP marketing kiosk", Drug Store News, Nov. 1991, 2 pages.
Warner et al., "Distributed medical intelligence, a systems approach for developing an integrative healthcare information distribution infrastructure", Institute for Interventional Informatics, Jan. 1996, 2 pages.
Warner, "The webification of medicine: inerventional informatics through the WWW", Med Wide Web, Jan. 1997, 2 pages.

* cited by examiner

COMMUNITY BASED MANAGED HEALTH KIOSK AND PRESCRIPTION DISPENSEMENT SYSTEM

CROSS-REFERENCES TO RELATED APPLICATIONS

This application claims priority from U.S. Provisional Patent Application No. 61/070,309, titled "HEALTH INFORMATION AND SCREENING SYSTEM", filed Mar. 21, 2008. This application is related to co-pending U.S. patent application Ser. No. 12/407,623, filed Mar. 19, 2009, titled "COMMUNITY BASED MANAGED HEALTH KIOSK AND REMOTE DIAGNOSIS SYSTEM"; U.S. patent application Ser. No. 12/407,637, filed Mar. 19, 2009 titled "COMMUNITY BASED MANAGED HEALTH KIOSK SYSTEM"; U.S. patent application Ser. No. 12/407,648, filed Mar. 19, 2009 titled "SECURITY SYSTEM FOR A COMMUNITY BASED MANAGED HEALTH KIOSK SYSTEM"; U.S. patent application Ser. No. 12/407,652, filed Mar. 19, 2009 titled "COMMUNITY BASED MANAGED HEALTH KIOSK AND RESEARCH DATABASE SYSTEM"; U.S. patent application Ser. No. 12/407,677, filed Mar. 19, 2009 titled "COMMUNITY BASED MANAGED HEALTH KIOSK SYSTEM FOR SOLICITING MEDICAL TESTING AND HEALTH STUDY PARTICIPANTS"; and U.S. patent application Ser. No. 12/407,682, filed Mar. 19, 2009 titled "TRIAGE BASED MANAGED HEALTH KIOSK SYSTEM".

BRIEF DESCRIPTION OF THE INVENTION

The present invention is directed to community based managed health kiosks and prescription drug dispensing systems, and more particularly to facilitating automated drug dispensement by a kiosk system following authorization by a remotely located health care professional monitoring a patient via the kiosk system.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Publicly available self-directed health care stations have been available at varying levels of complexity and sophistication for many years. Do-it-yourself blood pressure monitoring stations are often available in or near retail pharmacies, doctors' offices, corporate facilities, and retail centers such as shopping malls and strip malls.

The field of medicine has long employed health care screening to diagnose and track patients' health. An annual physical examination is a well-known part of patient medical care.

Hospitals, health clinics, and pharmacies, in addition to having an active role in supplying medical supplies and pharmaceuticals, have actively promoted various health care screenings and wellness programs. Screening programs are sometimes offered with the help of other health care providers or coordinated on a national basis with groups such as the American Lung Association, the American Diabetes Association, and the American Podiatric Medical Association.

Health care screening devices in hospitals, physician's offices, businesses, and the like, in combination with the growing number of home diagnostic kits that are available have increased the efficiencies in health care delivery. Large drug store operators have increasingly encouraged individual testing by making available in-store diagnostic testing devices. For example, customers waiting to fill a prescription are often encouraged to check their blood pressure while they wait with a blood pressure measurement/screening device, and pharmacists who fill high-blood pressure prescriptions to customers often encourage their customers to regularly check their blood pressure. Such customers often use blood pressure measurement/screening devices that are provided in the drug store.

To increase attention to the importance of health care screening, many medical and health product retailers offer medical tests and screening for consumers visiting their stores. Most commonly, the retailers check cholesterol levels and blood pressure, although other tests are available. In addition to supplying a valuable customer service, in-store testing effectively educates consumers about various health problems that can be better managed by a regimen that includes monitoring. Typically consumers are unaware of the technological advances that have made health care screenings feasible in the clinical, retail, and home settings. Pharmacies and drug retailers have generally found that the availability of screening test devices in the stores increase traffic and cultivate customer loyalty.

The offer of in-store testing commonly is highly popular among customers and greatly boosts the number of people visiting the store. In-store testing is valuable for positioning stores as health and wellness centers as well as retailers of health care products. In-store testing increases sales since a consumer who learns of a health problem through screening in the store has some likelihood of purchasing a home test kit to monitor the problem. For example, a customer who discovers a problem with high blood pressure through an in-store test is a likely candidate to purchase a home blood pressure testing kit.

In-store health care screening expands the pharmacist's role in patient care through education. Test device manufacturers have advanced the design and functionality of products to simplify usage and improve accuracy. The challenge for further improvements in health care screening is to educate consumers about the need for medical tests, and demonstrate that many tests are effectively performed by publicly available devices or at home.

A present concern is that health screening is performed on an insufficient segment of the population to efficiently prevent or treat ailments. Other concerns are that health screening is too costly, limited in scope, and time-consuming both for individual patients and health care providers. Despite these deficiencies, a strong awareness exists of a need and desire for improved health screening procedures and equipment. Health care providers, insurance companies, and employers that ultimately pay for health care have encouraged development and usage of improved, accurate, yet economic health screening facilities both for treatment and prevention of health care problems.

Generally, individual doctors and small groups of doctors have insufficient capital to maintain complete health screening facilities. Even if more health care providers were suitably equipped, typically only a small portion of the population utilizes health screening facilities due to time constraints, cost considerations, and/or general apathy.

Health care costs are a major concern in this day and age in the United States. Some commentators point out that our current national health care policy does little to incentivize preventative medicine and instead incentivizes treating major problems, at a high cost, somewhere down the line. More and better screening of patients, early and often, increases the likelihood of finding a problem early and treating it inexpensively, as opposed to finding it later and spending significantly more to correct a major health problem.

As health care costs go up, a doctor's time is also more valuable. It would be advantageous, and would save money, to allow doctors to see more patients each day.

What are needed are health screening devices, facilities, and methods that can be placed in locations that are convenient to health care customers. Suitable locations include retail outlets such as pharmacies or drug stores where customers already make health care purchases, but also may include medical offices, clinics, emergency rooms, hospitals, convalescence and elderly care facilities, work places (such as offices or factory sites), college dormitories, and the like. Health screening devices, facilities, and methods that are convenient, efficient, low in cost, and professionally accurate in screening health care data would greatly improve the general population's health.

Health screening facilities do exist. Bluth et al., U.S. Pat. No. 6,692,436 describes a health care information system including blood pressure monitoring and body weight monitoring. Such systems, however, do not take advantage of more modern technologies. More and more medical testing devices have become cheaper and easier to manufacture, making their absence from such screening facilities inefficient.

Local health screening facilities that take advantage of various medical testing device efficiencies and improved twenty-first century interconnectivity through the use of broadband Internet would be advantageous.

DETAILED DESCRIPTION OF THE INVENTION

Figure 1:
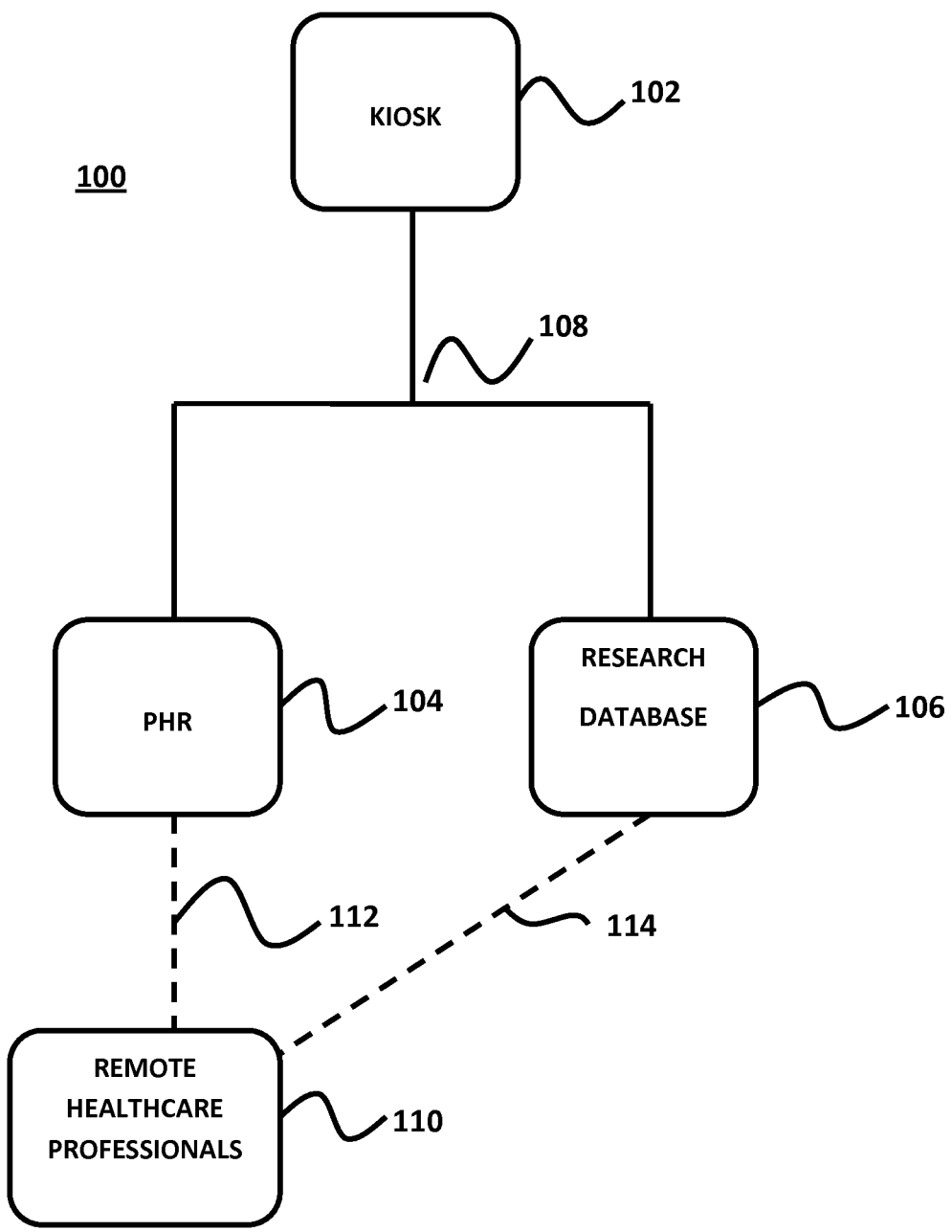
FIG. 1 illustrates the high level architecture of a managed health system or community-based health information and screening kiosk system in accordance with the research database embodiment of the present invention.

The following description is directed to a community based managed health system that includes a managed health kiosk system, a security system for the kiosk system, a research database system associated with the kiosk system, a prescription dispensement system for the kiosk system, a kiosk system for solicitation of patients for medical testing and health studies, and a triage based kiosk system.

The systems, and related methods, facilitate measurement, recordation, analysis, and communication of various health-related data belonging to a patient, many individual patients, or a specific group of patients. The system and/or apparatuses are able to measure, record, analyze, and communicate data from non-invasive and invasive testing from a variety of input devices. The herein disclosed invention can be a system, a method, or an apparatus, and involves a combination of computer and medical device hardware, computer and input device software, and physical kiosk hardware. The embodiments, however, will mostly be referred to as managed health systems or kiosk systems throughout this application for ease of reading.

The disclosed systems combine two or more input devices with one or more personal computers plus Internet connectivity to create a kiosk that a patient is able to use to further the patient's understanding and knowledge of his or her own health and to obtain professional health services. The system is able to utilize up to 24 external devices interacting with one or more personal computers and necessary software to measure, record, and/or analyze a patient's blood pressure, weight, heart rate, pulse oximetry, spirometry, resting metabolic rate, glucose, cholesterol, urinalysis, and other conditions. In other embodiments it may even be possible to utilize more than 24 external input devices. Each of these input devices receive pieces of health information from a user and facilitate recordation of the pieces of health information. Each will be explained below.

The herein disclosed managed health system or community based health information and screening kiosk systems can be equipped with a health risk appraisal platform. Such a platform can be utilized in many related ways. For example, a health risk appraisal platform can be used in a hospital emergency room for triage analysis. In such an application, a triage nurse will interact with the community based managed health system kiosk system and with the patient to determine the relative urgency of the patient's situation and what exactly may be afflicting the patient. In another example application, a community based health information and screening kiosk system can be located at an employer's offices or plant. In such a situation, employees are able to easily keep abreast of many of their own health risks and needs without having to take time off work to see an off-site doctor directly. Employers too may take advantage of the on-site kiosk to monitor and analyze aggregate (non-patient identifiable) health status data. In yet another example application, a community based health information and screening kiosk system can be located in remote or under-serviced geographic locations to allow patients to receive medical testing, information, and advice without having to travel long distances to see competent health care providers. Finally, aggregate data from one or more networks of community based health information and screening kiosk systems can be analyzed and then utilized to establish or monitor populations or geographic areas with greater disease risks.

The community based health information and screening kiosk system may be set up in different ways depending on the desired application. For example, at a minimum, different prompts will be displayed to an emergency room triage patient, compared to an employee using a company on-site kiosk to obtain a monthly health evaluation. It may also be that entirely different combinations of medical testing and input devices are appropriate for each of the different community based health information and screening kiosk system applications. All such input devices and software variations will be explained below. As will be apparent to those skilled in the art, all such permutations are possible and are intended to be covered by this disclosure. If certain embodiments describe certain permutations, it is because such permutations appear to be either a minimum for the desired application, or it is because such permutations appear to be ideal for the desired application. But in every instance, all such permutations are intended to be within the scope of this disclosure.

One embodiment of the herein disclosed community based health information and screening kiosk system includes a health risk appraisal platform. This platform is able to display to a user a series of computer screens which present a set of health data, including health information and health assessment questions designed to obtain health and lifestyle information from the user to enable the platform to assess health risks.

The health risk appraisal system can be either a platform or a specific software program. It is possible to design the overall community based health information and screening kiosk system so that an individual user can pick and choose how the appraisal system elicits health, biographical, and lifestyle information from a user. In such a situation, the owner of the overall system (the kiosk) would be able to select questions from a predetermined list or may be able to write his or her own questions. Such an owner may also be able to choose the order in which such questions are presented. Such a platform is fully adjustable, editable, and customizable by a sophisticated owner, allowing unlimited options for the owner to elicit patient/user information. It is also possible to design the disclosed health risk appraisal system as a pre-packaged software program, or as several fully thought-out, pre-packaged software programs.

The appraisal system is able to utilize either a touch screen or a keyboard and mouse/trackball setup, or even a combination of a touch screen and a keyboard. These devices can be referred to as control devices. With a touch screen built into the system, a user is able to select answers to multiple-choice type questions directly onscreen. With a keyboard and mouse as user-input devices for the system, a user is able to more easily personalize a response. Detailed answers could be typed out as phrases, full sentences, full paragraphs, or even multiple paragraphs. As information will be stored digitally and/or electronically, there is no inherit need to limit space for a user or patient's explanation of health related information. To reduce the need to sterilize the user touched components of a kiosk system, voice recording or recognition software could be utilized so a user is able to speak answers to questions.

As discussed above, the system can be built pre-programmed with packaged health risk assessment question sets. There are many such health risk assessment tests available in the medical and health community. One such example is the PHQ-9 (Patient Health Questionnaire) assessment test. This is a nine question, relatively detailed test. The PHQ-9 is a powerful tool for assisting primary care providers in diagnosing depression as well as selecting and monitoring treatment, and is based directly on the diagnostic criteria for major depressive disorders in the Diagnostic and Statistical Manual Fourth Edition (DSM-IV). There are two components of the PHQ-9: assessing symptoms and functional impairment to make a tentative depression diagnosis; and deriving a severity score to help select and monitor treatment. Many other such pre-packaged health assessment tests are available and can easily be formatted for use in the disclosed health risk assessment system.

Aside from highly interactive embodiments of the disclosed health information and assessment system, the disclosed invention may also be utilized by a user, or optimized by the owner for specific or known users, as a type of health information encyclopedia. In this sense, the system may be utilized like a personal computer accessing a specific website. A user is able to navigate a complex combination of health information screens and menus that allow the user to find information on any health-related topic that may be of interest.

Such an encyclopedic embodiment may be able to display all sorts of health related data. For example, the system may be able to provide information on various vitamins, minerals, drug active ingredient listings, drug use directions, drug interaction warnings. The system may be able to provide videos on preventative and/or healthy living practices like exercise, ideal sleep patterns, and health-sustaining diets. The system may also provide local directories of community health care providers and services in the user's hometown. All such health information can be locally stored at the kiosk system on a hard drive or on a standard media format such as a flashdrive, a CD, a DVD, etc, or remotely at a personal health record storage system or a remotely located website.

The disclosed health information and assessment system may be able to display information, health questionnaires, health assessments, and other important information in practically any language. Such an ability to display in multiple languages is obviously of value, even if such systems are only used in the United States. According to a 2006 American Community Survey conducted by the United States Census Bureau, Spanish is the primary language spoken at home by over 34 million people aged 5 or older. Obviously, it is desirable to obtain, and dispense, accurate health and fitness information with the disclosed system. Providing health information and presenting health questions in a user's native language will help to increase a user's understanding and ensure that more accurate information is provided to the user. This is easily done with the disclosed system.

The number of available display languages is only limited by the software components which are used to build the system, and by the investment that an owner is willing to make having health information and questions for the system owner translated.

Aside from display considerations, how the system stores information is of great importance. The health information and assessment system may be able to provide a rough instantaneous translation of information input by a non-English speaking user (or a user who speaks English, but for convenience has chosen to interact with the system in his or her own native language). In this way, user-supplied non-English answers to open-ended questions (as opposed to multiple-choice questions) can be processed and automatically translated into English before being sent to medical professionals such as nurses and doctors. Such processing of multiple-choice type assessment questions is obviously much more easily handled—both questions and each available answer can be pre-translated so that a user is essentially answering each question in all available languages at once.

Instantaneous automatic translation, which is referred to as machine translation in the field, is not today as accurate as human translation. Nevertheless, machine translation is available that does a passable job that may be good enough for emergency-type situations. Such machine translation can be assisted by producing the original text to be translated in what are referred to as controlled natural languages. Controlled natural languages are subsets of natural languages, obtained by restricting grammar and vocabulary in order to reduce or eliminate ambiguity and complexity. The health information pages and the assessment questions can be originally drafted in controlled, or simplified, English so that it can later be automatically machine translated by the system. Non-English users can be advised to use simple and straightforward sentences, while avoiding slang, when inputting their answers.

Information obtained by the health information and assessment system about a user is stored for the user's convenience, for use by health care providers, and for research purposes. The health information is securely stored so that there is no fear of unauthorized dissemination of user health information. The stored information is a combination of user-input answers to health assessment questionnaires and results from various intrusive and non-intrusive health analysis procedures, which will be described in detail below (cholesterol testing, for example). These may be referred to as pieces of health information and pieces of personal identification information (or personally identifying information). This combination of user health information is referred to as a PHR, which stands for Personal Health Record.

The PHRs can be stored in a number of ways. An exemplary embodiment of such a health information storage system is where the PHR, gathered at a health information and assessment kiosk system, is transmitted to a storage and processing server located off-site, meaning at a geographic location different than where the kiosk itself is located. The transmission of PHRs may be accomplished through use of a private network, or a public network, such as the Internet. When a public network is utilized, the PHRs are encrypted or otherwise secured so the privacy of the user's health information is maintained, such as through the use of secure socket layer (SSL) formatting, as is known in the art. When a public network, such as the Internet, is utilized the PHRs may be stored at a nation-wide hub, or multiple regional hubs, to reduce storage and transport costs, to facilitate access to the information from authorized sources, and to provide a level of redundancy to avoid a catastrophic loss of the information. It is also possible for the user to dictate where his or her PHR should be stored. For example, third parties may setup PHR deposit websites configured to receive, store, and make available a user's PHR created by the herein disclosed kiosk system. Or, it may be possible for the user to dictate that such information be sent, via email or ftp or another appropriate electronic information transmission system, to user's website or personal computer for storage as the user sees fit.

Regardless of where a PHR is stored, the PHR is ideally always available for review by the user at a later date. For example, once a user has input his information at a kiosk system, that user can later access the information at the same kiosk or at another kiosk at another geographic location. The security measures of the present invention ensure that a user attempting to access a PHR is in fact the correct user, but such information is always available once input.

When stored for research purposes, health information is aggregated and not stored like PHRs. With aggregated information, unlike a PHR, health information is not grouped together by user. Instead, data from each distinct test or question is grouped with other user's data in an aggregated database to allow for study of trends throughout populations. Aggregated data from multiple users, or groups of users, may be researched, but a specific individual's PHR is not accessible by the researcher(s). One exemplary way of doing this is to assign each user an identification number, and then assign that number, instead of the user's name, to each piece of health data or health information obtained from that user. Authorized entities (researchers) studying the aggregated data would be unable to connect an identification number back to the user's name, thus preserving a user's confidentiality and privacy. Authorized entities would, however, be able to sort the aggregated database by various appropriate parameters, such as: disease, treatment, geographic regions, user demographic (user age, gender, ethnicity, etc.) or classification (employee type, etc.). The research database may be capable of extracting such parameters, including demographical and/or classification information, from the personally identifying information so that the various pieces of health information can be organized or sorted by the parameters without linking the pieces of information to individual users' names or identities.

FIG. 1 illustrates a layout of the herein disclosed community based health information and screening kiosk and research database system. Kiosk and research database system 100 includes a kiosk system 102 that is connected to both the user's PHR 104 and research database 106 over a network, such as the Internet, 108. When a user uploads his or her health data, it is recorded and analyzed at kiosk system 102, simultaneously incorporated into the user's PHR 104 and incorporated (in a non-personally identifiable way) into research database 106. Remotely located health care professionals 110 would have the ability to access the user's PHR 104 if the user allows such access (dotted line at 112 represents user's ability to control when and how health care professionals can access the user's information). Dotted line 114 represents that research database 106 can be accessed by remote health care professionals, including researchers world-wide, and can be manipulated in various ways. For example, aggregate user data can be filtered by disease, by treatment, by user statistics/demographics (such as user age, gender, etc), etc.

A user's PHR, and the individual data points being stored for research in the aggregated form, are maintained with the user's confidentiality and security in mind. All record storage meets or exceeds privacy standards, including HIPAA (Health Insurance Portability and Accountability Act), a federal statute governing maintenance of electronic health records.

In addition to security means for securing transmission of data, many physical security means can be used at the kiosk site to provide security. Up to five levels of security can be implemented in the disclosed health information and assessment system. The security measures can include the following identity verification devices: a thumbprint scanner, a signature pad, use of photo identification cards, an access card with a 16-digit magnetic stripe, and a 4 digit PIN (Personal Identification Number) set by the user. These identity verification security devices will be discussed below. The five levels of security can be combined in various ways. For example, a kiosk system could require at least two forms of identification (a matching thumbprint and a PIN number, for example) from a user before the user is able to access a PHR through the kiosk. The five levels of security can of course be combined in other ways and this specification intends to include all such permutations.

As described above, the herein disclosed health information and assessment system has the ability to store aggregated user health information and data for analysis. Such analysis can be contracted out to a third party, or such analysis can be part of the entire system. For example, a company that chooses to locate a health information and assessment kiosk system on its premises can mandate, or suggest, that its employees regularly complete a health assessment questionnaire. Results from all company employees can be analyzed in aggregate form to evaluate the company's employee's overall health and fitness levels, and can be used to spot trends, both positive and negative.

Such an analysis can be done on aggregate data for many purposes. For example, such an analysis may assist a company in comparing the health of its employees from office to office or from one production facility to another production facility. Other exemplary analyses that can be done include assessing health status data according to employee classification and determining frequently occurring diseases or ailments.

The disclosed health information and assessment system is able to perform more generalized employee surveys, beyond health assessments. For example, employers who place a health information and assessment kiosk system at their workplace can ask employees to answer questions regarding their job satisfaction and/or to provide suggestions for company improvement. The kiosk system can be useful in this regard for companies whose employees are not regularly interacting with computers and so can not otherwise easily take automated surveys. As with health assessment questionnaires, employee surveys can be designed by the company itself or can be chosen from many pre-packaged employees surveys available in the field.

If a company's employees do not have regular access to a computer, the health information and assessment kiosk system can also provide Internet access to employees. Essentially, because the kiosk system incorporates at least the major components of a personal computer, the kiosk system can easily accomplish many common personal computing tasks, such as word processing, email, and Internet browsing. A company may find it useful to provide the kiosk system for these personal computing uses if their employees do not otherwise have regular access to a personal computer. It also is possible for the company to limit the available webpages that a user can navigate to while using the kiosk system for Internet-browser activity. A company could, for example, limit Internet browsing to only the company's own website. Or, the company could set up its own custom firewall, or chose a pre-packaged firewall, to limit employees to only browsing those sites pre-approved by the company.

Due to the large amount of data collected, especially when video is utilized, many of the applications herein disclosed require some form of network connectivity, but this can be both internal to and external to the kiosk system. The kiosk system itself may be connected to a network through a network connection, which may be a standard 10/100 Mb Ethernet jack (RJ45) through a local LAN network or a direct connection to a storage system that is resident within the kiosk system, physically located nearby, or remotely located. Alternatively, kiosk systems may be equipped with 802.11a/b/g devices for wireless connectivity, with storage being nearby or remote. Other methods or devices for connecting with a network are known in the art and may also be appropriate.

As described above, the health information and assessment system is able to accurately obtain a user's vital signs through a combination of invasive and non-invasive testing. The data from the various invasive and non-invasive testing procedures can be stored as part of the user's PHR, and it can be transmitted to health care professionals at other geographic locations. In many situations, such as prior to or following a major medical procedure, a doctor would like to closely and accurately monitor a patient's vital signs, such as body temperature, pulse or heart rate, blood pressure, and respiratory rate, without requiring the patient to go to a doctor's office or a medical facility. All of these vital signs, and many more health metrics, can be monitored remotely using the health information and assessment system, which may be located at a community clinic, at a drug store, at a grocery store, or many other convenient locations close to a patient's home. A doctor or nurse is then able to receive an electronic transmission of the desired vital sign data, and other data, so that the doctor or nurse can monitor the patient's vital signs remotely, and even communicate directly with the patient while the kiosk system is in use, as further described below.

Such a remote monitoring setup is desirable for many reasons. The doctor or nurse is able to remotely monitor several patients, possibly at the same time, from one centralized location without having to travel. Conversely, the patient is able to avoid the need to travel, what may be a long distance, to see the doctor or nurse, and can instead travel, what may be a short distance, to a local health information and assessment kiosk system.

Figure 2:
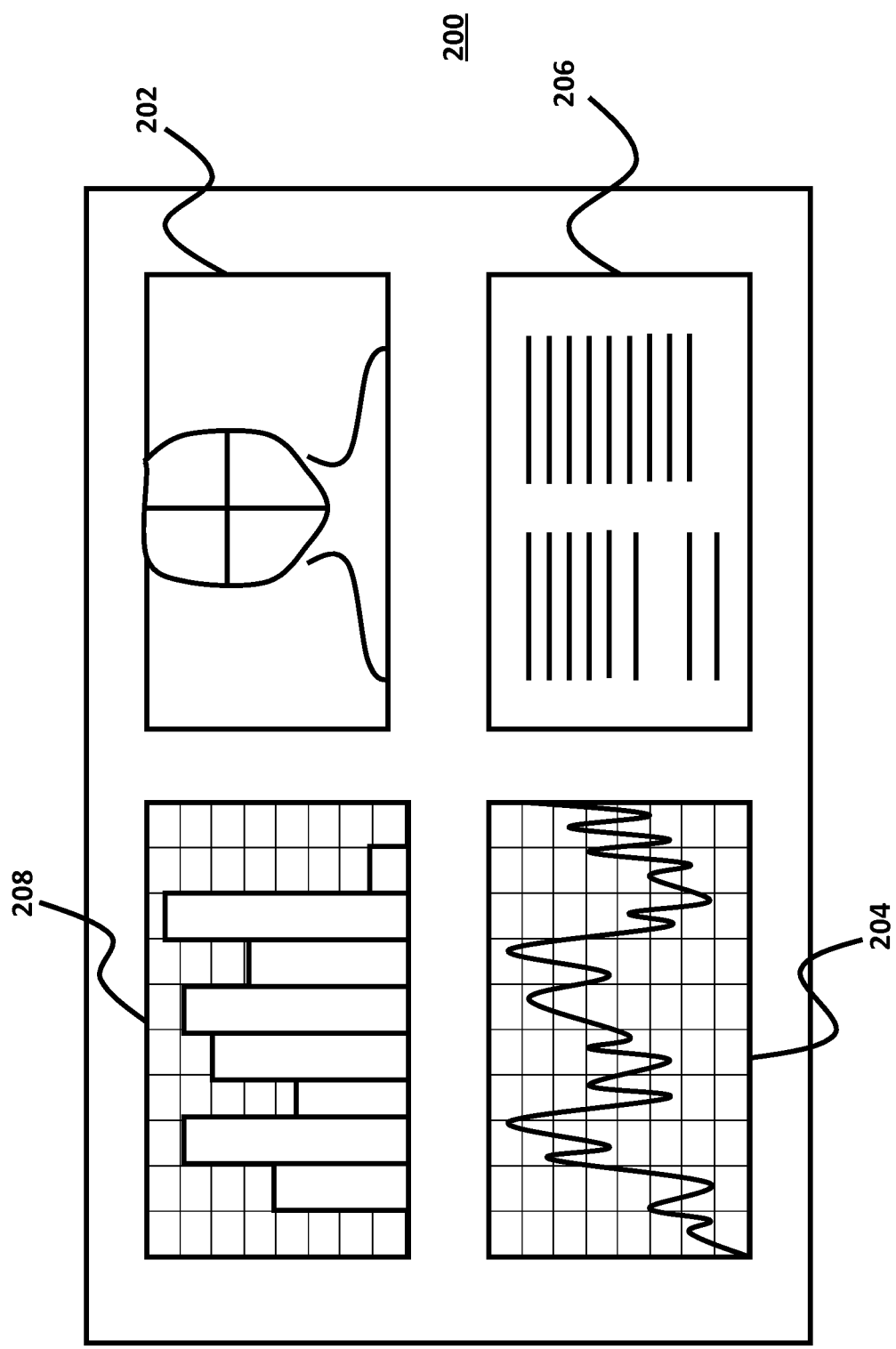
FIG. 2 illustrates a user-data screen from the perspective of a remotely located health care professional in accordance with the present invention.

FIG. 2 illustrates a user-data screen 200 as displayed to a remotely located health care professional in accordance with the present invention. When a user is interacting with a remotely located health care professional, the user's video image 202 and the user's health data can be simultaneously displayed to the professional. User-data screen 200 may include live video 202 of the user on one portion of the user-data screen 200, include wave-form user data 204 (blood pressure readings, for example) on another portion, textual user information 206 (personal information such as name, age, etc, for example) on another portion, and possibly further user data 208 on another portion. In this way, a remotely located health care professional can fully interact with the user seated at a kiosk system. The remotely located health care professional may be able to select which pieces of health information are displayed by user-data screen 200. Additionally, the user-data screen 200 may be combined with a health care professional video camera to capture a video image of the health care professional, which then may be displayed to the kiosk user. This user interaction with a remotely located health care professional is sometimes referred to as telehealth in the medical community. The herein described kiosk system enables greatly enhanced telehealth because live patient/user video, real time vital sign readings, and additional detailed user health information can be combined with traditional voice interaction (a user communication and a health care professional communication can be sent back and forth between the kiosk system and the remotely located user-data screen system) to allow health care professionals to conduct appointments, screenings, and diagnoses over long distances easily and efficiently.

The herein disclosed community-based health and screening kiosk system can also act as a community, or even a larger geographic area (such as a nation-wide), health analysis tool over a long term time frame. For example, the data collected from users and patients can all be stored either locally or remotely at a centralized location as described in FIG. 1 above. This information is aggregated so that it is no longer identified with the individual who provided the data. This information can be accumulated over long periods of time from a vast number of users or patients. All this aggregated health data can be very valuable to the greater medical community. The data can be analyzed and trends can be identified over time.

An additional application of the herein disclosed kiosk systems is to provide live video for verbal discussions between users and remotely located doctors. This application creates the opportunity for automated prescription drug dispensement from the kiosk system. A remotely located doctor can view the patient, talk to them about their issues and needs, and obtain all the health data he or she needs to legally and ethically write a drug prescription for the patient. The kiosk system may be equipped with several of the most widely prescribed drugs in an automated dispensing device. Such auto-dispensement devices are known in the art, but have never previously been combined with a real-time remote health assessment and analysis system. Existing dispensement devices made by companies such as QUIQMED, PHARMACY AUTOMATION SYSTEMS, and INSTYMEDS can be advantageously combined with the herein disclosed kiosk systems to produce a community based managed health kiosk and prescription dispensement system. Such commercial drug dispensers, and their equivalent, may be capable of measuring a prescribed amount of the prescription drug and then bottling this prescribed amount in a consumer container, such as an industry standard cylindrical plastic container. Alternatively, such prescription dispensement devices may dispense blister packs, containing pre-dosed amounts of the prescription drugs, as is known in the art. It may be additionally possible to attach a payment system to the managed health kiosk and prescription dispensement system. Such a payment system may be capable of receiving payment by cash or by credit or debit card, as is well known in the art. Alternatively, the kiosk system can be combined with a prescription printing device, which may be a standard computer printer, for printing industry recognized drug prescriptions. Or, the kiosk system can be located in a commercial or public pharmacy facility, in which case the kiosk system may be capable of receiving the drug prescription from the remotely located health care professional and transmitting it to the pharmacy facility, where the prescription can be filled.

A further application of the herein disclosed kiosk system is in the solicitation of medical testing and studies volunteers. As described, the kiosk system is able to measure and record all sorts of health information of users. Once a health assessment has been performed on a user, the kiosk systems can go one step further and compare the user's individual health to databases of on-going or upcoming medical tests and studies. The medical community has a difficult time finding testing subjects for very specific tests because there is a disconnect between the medical professionals looking for test subjects and the people with the diseases and conditions they are looking for. Once a user completes a health screening at the kiosk system, however, he or she can be immediately made aware of upcoming tests and/or trials that might be appropriate for that user. The user can be shown these tests and trials on user-display screen 406. Going further, the user can then direct the kiosk system to send, over the kiosk system network 108, an application for the test and/or trial.

Figure 3:
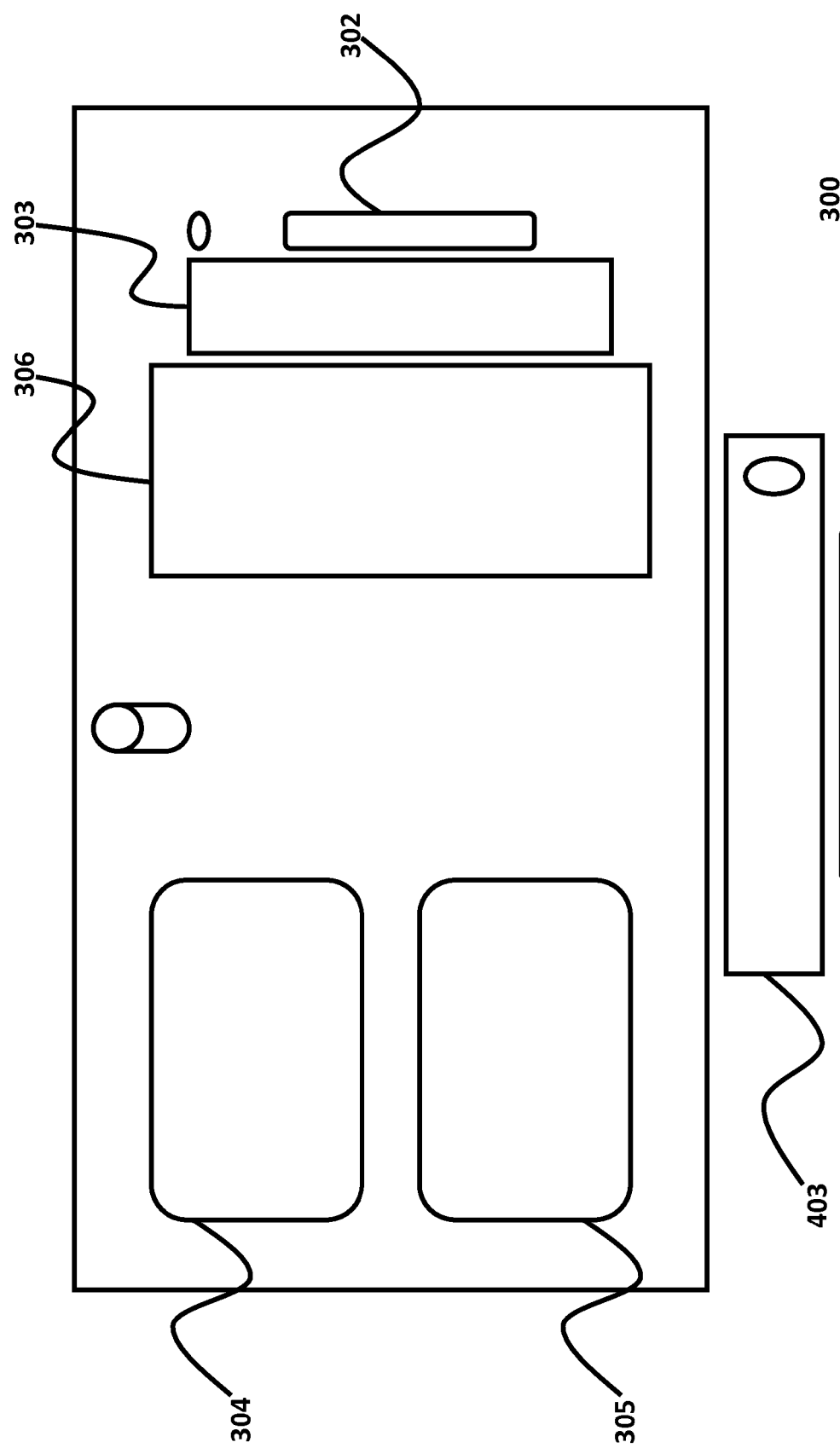
FIG. 3 is a plan view of a community-based health information and screening kiosk system in accordance with the triage embodiment of the present invention.

As described above, kiosk systems may also be used in triage situations. In such situations, a kiosk system may be located in an emergency room or the waiting room of a clinic, where patients can sit down (if they are able to do so) and communicate with the kiosk system to provide information regarding their condition. An on-site nurse or other health care professional may then work with the kiosk system to determine the user's relative health situation; i.e. whether and when the user needs professional care. As further described below, FIG. 3 illustrates a plan view of a portion of a kiosk system designed for triage use. In addition to the user's monitor and input devices (user-display screen 406 is not visible in FIG. 3, but keyboard 403 and signature pad 402 can be seen and indicate where the user would sit), triage kiosk 300 may have an additional health care professional keyboard 303 and health care professional signature pad 302. Additionally, the health care professional may have his or her own health care professional monitor 306, separate from user-display screen 406. Those skilled in the art will recognize that a laptop PC, or standard stand-alone PC, could be used in place of health care professional keyboard 303, health care professional monitor 306, and/or health care professional signature pad 302, in what may be referred to as a health care professional input and display system. These health care professional input devices allow an on-site health care professional, such as a triage nurse, to monitor the user's progress through a kiosk health assessment questionnaire, and so sign-off on (or deny) the results of such an assessment or completed questionnaire. In other words, the health care professional can assess the completed questionnaire and provide his or her health care professional authorization for a final triage assessment.

In such triage situations, the kiosk systems can be combined with a printer to print out situation-specific user-identifying labels. The labels may include a triage assessment and can be worn by the user to convey the user's triage assessment to other health care professionals working in the emergency room or clinic.

FIGS. 2 through 5 illustrate many of the various embodiments of the disclosed community-based health information and screening kiosk system. The kiosk system has many different components that can be used in many of the different embodiments, but may not be needed in others. Hence, a great variety of different permutations of the kiosk system, each including different combinations of those components, could be developed. For example, the kiosk system can include headphones, a microphone, a keyboard, a card reader, a signature card, a thumbprint pad, a scanner, a privacy curtain, a release button, a camera, glucose meter hook-up, a pulse oximeter, weight-scale, blood pressure monitor, invasive-testing inputs, a temperature sensor, and other testing devices. These devices may then be combined with various other devices, such as a printer, an audio speaker, a video display screen, and/or Internet connectivity. Each of these devices can then be integrated into the software platforms so that data received by the input device can be incorporated into a user's PHR and/or delivered in useful format to a health care professional.

A preferred embodiment of a kiosk system is described with reference to FIG. 4. The kiosk system of FIG. 4 has a user desk portion 400 that includes a number of different items, include headset 401, which may be a physical combination of headphones and a microphone, or the functional combination of a pair of headphones and a microphone separately mounted within the kiosk system. Headset 401 allows a user to communicate with a health care profession and hear audio information dispensed either from a remotely-located health care professional or from available pharmaceutical encyclopedias and/or health information videos and the like. Headset 401 could be comprised of a flexible band and wiring that feeds audio content directly into a user's ears through one or two speakers held against the user's head by the band, while also being capable of receiving audio input by the user via a microphone. It could also be a standard telephone-type input/output device—having a u-shaped hand-held plastic or metal piece that a user holds up to the side of his head, while placing the speaker at the user's ear and the microphone near the user's mouth. Headset 401 allows the user to interact with remote health care professionals by speaking a user voice communication into the microphone and by listening to a health care professional communication through the headphones. Obviously, speakers mounted within the kiosk could be used in place of the headphones. The advantage to using a headset is that it leaves a user's hands free to simultaneously use other input devices, such as the keyboard or the pulse oximeter.

Signature pad 402 may be located on the user desk portion 400 in front of, or slightly beneath, keyboard 403. Keyboard 403 is a standard alphanumeric keyboard that a user may use to input words, phrases, sentences, paragraphs, or even multiple paragraphs into the system. Keyboard 403 can additionally be utilized by deaf and/or hard-of-hearing users to communicate in real time with health care professionals. Such user inputs, or responses, may be integrated into the user's PHR, may be used as part of an automated health assessment, and/or may be transmitted to a remote health care professional to be used as the health care professional sees fit. Keyboard 403 is generally a standard United States layout keyboard (QWERTY setup), but a foreign-language keyboard or keyboard setup may be substituted as needed in foreign locations.

Signature pad 402 may be a standard signature pad for electronically recording a user's signature. A user may be prompted to enter his or her signature into signature pad 402. A user's signature may be used as a security measure, to compare with a previous signature in a user's PHR, or may be used in a legally binding way to create a contract or to acknowledge a doctor's warning, etc. Many commercial signature pads are available on the market, and most can be utilized in the disclosed kiosk system. Such signature pads have a relatively small LCD, or equivalent, display screen, and a pen-like device that the user uses to write his or her signature on the small display screen. The movements of the pen-like device are recorded by the signature pad and then can be transmitted into the kiosk system. An image of the user's signature can be stored at the kiosk, or can be transmitted to remote health care professionals or to the user's remotely-stored PHR.

Thumbprint reader 410 may be located on the right side of the user-desk portion 400 of the kiosk system. Thumbprint reader 410 is a commercially available device for capturing the likeness of a user's thumbprint. If the kiosk system is set up to utilize thumbprint reader 410 as an additional security measure, a user may be prompted to insert his or her thumb into the reader, or to swipe his or her thumb through, or past, thumbprint reader 410. As is known in the art, the thumbprint reader 410 may compare the user's thumbprint to stored thumbprints, or may compare portions of the user's thumbprint, such as specific swirls, whorls, or patterns within a thumbprint, to previously recorded thumbprint portions. Alternatively, if a user is utilizing the kiosk system for the first time, thumbprint reader 410 may record the user's thumbprint, or portions thereof, for future security-related comparisons. Alternatively, an electronic fingerprint identification system may be substituted in a community-based health information and screening kiosk system in place of thumbprint reader 410.

Card reader 405 may be located on the left side of the user-desk portion 400 of the kiosk system. Card reader 405 may be one or several types of commercially available card readers. Card reader 405 may be able to read magnetic stripe cards that store information/data on a band of magnetic material on the back of the card, such as a credit card or some identification cards, or may be able to read cards carrying information/data in the form of bar coding.

The overall system may be capable of creating user-specific health kiosk cards. The system may be able to print out a health kiosk card for a user that stores (magnetically, by bar code, or by an alternative data storage system known in the art) identifying information and the user's PHR. Card reader 405 may be capable of reading the user's data off one of these health kiosk cards, so that a specific user may easily transport his or her PHR from one kiosk to another. Such a card can also act as an additional form of identification for security purposes.

Camera 407 may be located above user display screen 406. Camera 407 may be a commercially available digital or analog video recording device capable of capturing static images as well as full motion video. In certain embodiments, camera 407 may be mounted on the end of a flexible and adjustable cable and be capable of being pulled out by a user. Fiber optic cables can allow for this sort of flexibility and adjustability and may be appropriate. For example, if a remote health care professional wishes to see a close-up image of a user's ailment, the user may be able to pull out camera 407 to give the health care professional a better image of the patient.

The main purpose of camera 407 is to capture still and motion images of a user, which are then transmitted to remotely located health care professionals. Still and/or motion images of the user may also be stored and incorporated into the user's PHR or for any other suitable purpose. User image 202 in FIG. 2 illustrates the view that a remotely located health care professional could see of the kiosk user.

User display screen 406 is located at the approximate center of vertical panel 412 of the user desk portion 400 of the kiosk system. User display screen 406 may be a standard video monitor capable of displaying full color still images and/or full motion video. In a preferred embodiment, user display screen 406 is a 15 to 17 inch color monitor with a touch screen. Touch screen capability allows a user to input selections and manipulate data by directly touching the screen, as opposed to having to use a mouse or keyboard to make on-screen selections, as is known in the art. A standard personal computer mouse (not shown) may be incorporated into systems not utilizing a touch screen.

Figure 5:
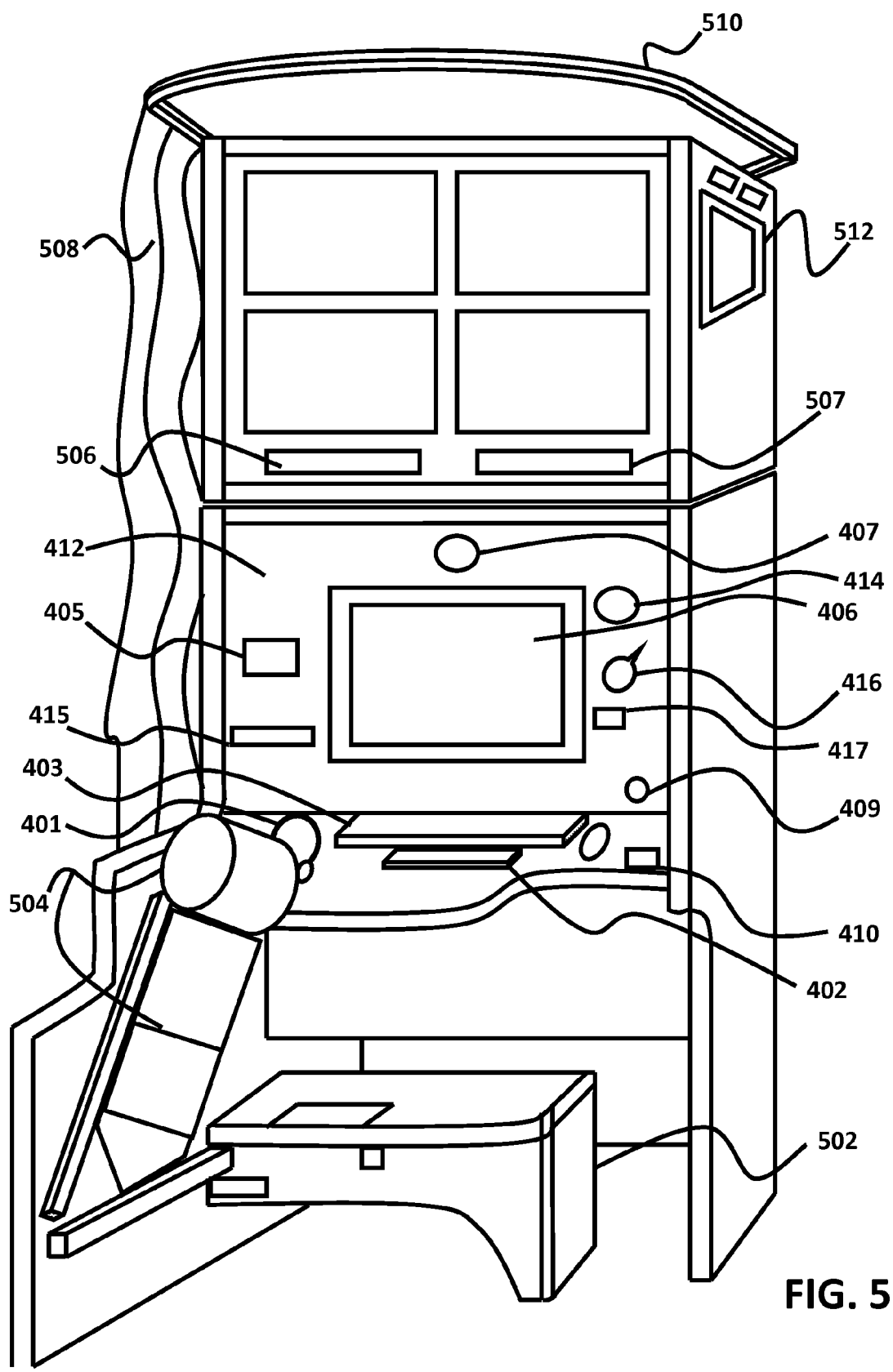
FIG. 5 is a perspective view of the front area of a community-based health information and screening kiosk system in accordance with the present invention.

Speaker 415 may be located anywhere on the kiosk system, so long as a user seated in user seat 502 of FIG. 5 is able to hear the audio emanating from speaker 415. As will be further shown in FIG. 5, use of the speaker 415 may be limited, however, in order to prevent someone from overhearing the questions being asked of the user and/or the user's answers when being provided or providing personal information. A privacy button is provided on the vertical panel 412, on the touch screen 406, or elsewhere within the kiosk system, to enable a user to switch from verbal communication via the speaker 415 and a microphone to the headset 401 or a traditional telephone headset (not shown). In a preferred embodiment, speaker 415 may be located on the left side of vertical panel 412 of the user desk portion 400 of the kiosk system. Alternatively, more than one speaker may be used. For example, two speakers, one on each side of user display screen 406, may be used to provide stereo sound to a user. Speaker 415 may be any sort of commercially available audio speaker capable of playing audio sounds produced by the kiosk system. Speaker 415 may be configured so that when a user plugs headphones or a headset 401 into the kiosk system, speaker 415 automatically mutes so audio only is played through the headphones or headset 401. Alternatively, the software platform may provide a user with various audio options, including allowing audio to play both through headphones/headset and through speaker 415. Those skilled in the art will recognize the various audio arrangements that are possible when a kiosk system is configured with both headphones/headset 401 capability and speaker 415 capabilities.

The following devices, and other similar devices, may be referred to as medical diagnostic devices, as they are used to record, measure, and/or analyze the user's health. Pulse oximeter 409 may be located near the bottom of vertical panel 412, to the right of keyboard 403. Pulse oximeter 409 should be located so that a user can easily insert his or her finger into the pulse oximeter while seated normally at the kiosk system. A pulse oximeter is a device used to indirectly measure the oxygen saturation of a user's blood (as opposed to measuring oxygen saturation directly through a blood sample) and changes in blood volume in the skin. Pulse oximeter 409 may be used to produce a photoplethysmograph (a possible output format of a pulse oximeter), which may be incorporated into the user's PHR, transmitted to remotely located health care professional, or otherwise stored and used as appropriate. Most commercial pulse oximeter devices clip onto a user's finger and send data through wires running back towards the user and along the user's arm. Pulse oximeter 409 may be designed so that its wiring runs back into and is communicatively coupled with the kiosk system, away from the user.

A temperature sensor 414 is provided in the upper right portion of the vertical panel 412, but could be located elsewhere. Any one or more of a number of different temperature sensors 414 could be used, such as a contact sensor that infers the temperature of a user that contacts the sensor, or a noncontact sensor that might use an infrared sensor, or some other form of sensor, to detect the temperature of a user in proximity of the sensor.

Blood glucose meter port 416 may be located anywhere on the kiosk system. In a preferred embodiment, blood glucose meter port 416 may be located below the temperature sensor 414 on the right side of vertical panel 412 of the user desk portion 400 of the kiosk system. Blood glucose meter port 416 is capable of linking to standard commercial blood glucose meters through interface hardware in the port, which may be situated on a cable to make it easier to connect to a meter. When a user hooks his or her blood glucose meter into blood glucose meter port 416, the data stored on the blood glucose meter is transferred into the kiosk system, where it can be incorporated into the user's PHR, transmitted to remotely located health care professionals, or stored and analyzed as appropriate. It is also possible to include a non-invasive blood glucose meter in the kiosk system, so that a user does not have to provide his or her own blood glucose meter.

Figure 4:
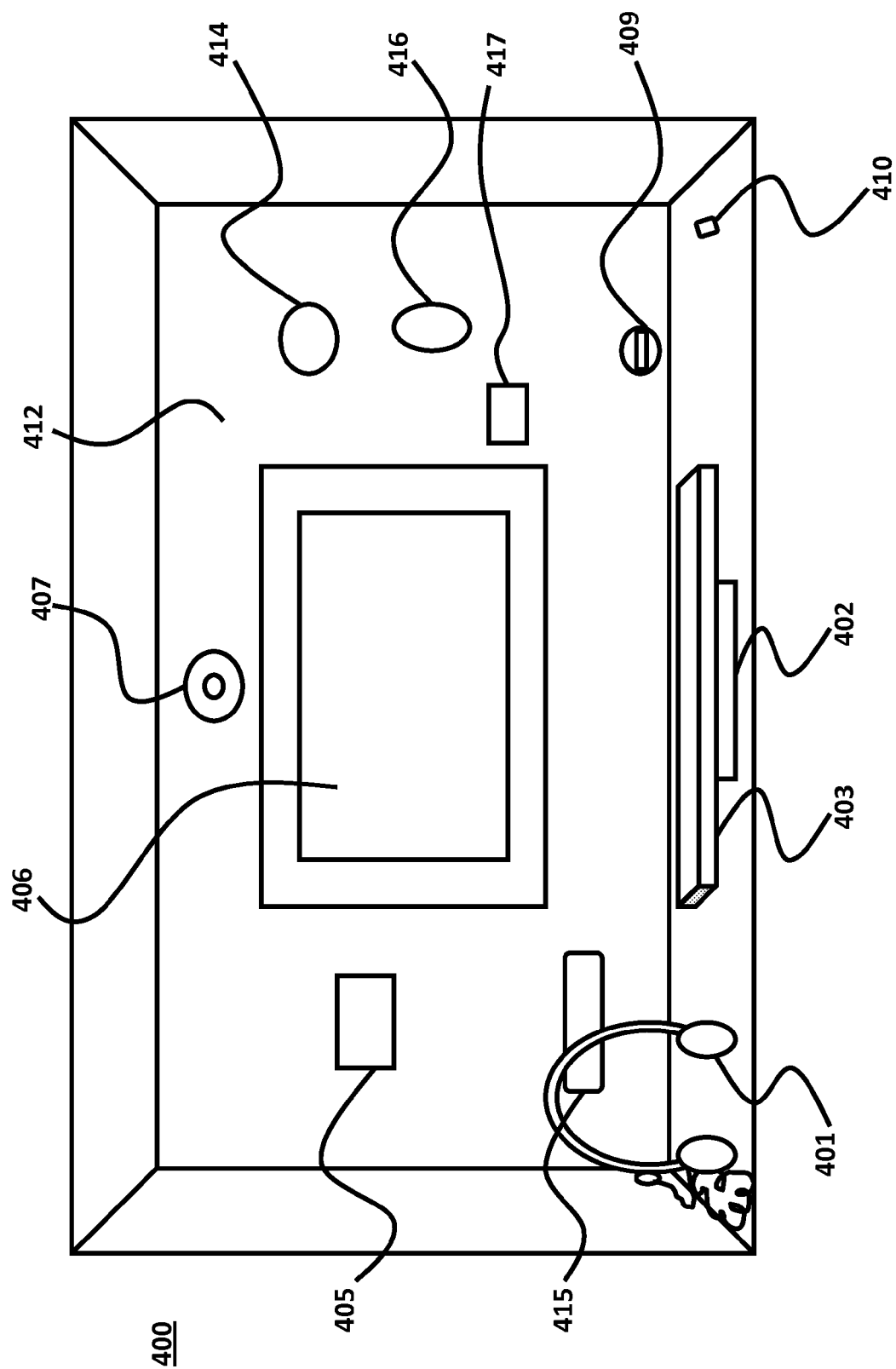
FIG. 4 is a perspective view of the user desk portion of a community based health information and screening kiosk system in accordance with the present invention.

Blood pressure cuff test interface 504 is not clearly seen in FIG. 4, but is illustrated in FIG. 5. Blood pressure cuff test interface 504 is positioned on the left side of the kiosk system, so that a user can easily slip his or her arm through the cuff while seated on the seat 502 of the kiosk system. Blood pressure cuff test interface 504 is capable of measuring and analyzing a user's blood pressure and heart rate. The blood pressure cuff test interface 504, in combination with the overall kiosk system, utilizes a measurement algorithm based on a plurality of measurements, providing a unique ability to increase diagnostic and analytical success in detection.

In an illustrative implementation, three measurement techniques are used in combination to improve overall measurement accuracy. A first of the three techniques is an ascultatory technique. A sound measurement acquired from a microphone located in the measurement cuff detects start and end Korotkoff sounds using a combination of filters. The auscultatory technique is a conventional method that is recommended by the American Heart Association and is similar to manual techniques used by a health care professional. The auscultatory technique and associated filtering techniques are well known by those having ordinary skill in the art. A second technique is an oscillometric technique that is commonly found in many low-cost blood pressure measurement devices. A pressure cuff is used to measure pressure oscillations, which are detected and monitored using mean pressure, and systolic and diastolic pressure ratios to identify systolic and diastolic blood pressure. A third technique, called a pattern recognition technique, measures a sound envelope and incorporates pattern recognition to identify systolic and diastolic pressures. The pattern recognition technique uses 1,000 sound impressions per second, or between 40,000 and 60,000 sound impressions per test. A signal from the pressure sensor is used in addition to the three techniques to quantify the regions of sound under analysis. The precise blood pressure cuff test interface apparatus and methods of use are described in Bluth et al., U.S. Pat. No. 6,511,435, which is incorporated herein by reference.

The blood pressure and heart rate data obtained by use of blood pressure cuff test interface 504 may be utilized in much the same way as other data collected from a user by the kiosk system. Such data can be utilized to perform a health risk assessment for the user, can be incorporated into the user's PHR, can be transmitted to remotely located health care professionals, can be transmitted to various medical research databases in a non-personally-identifiable format, and/or can be stored locally and analyzed as appropriate.

User seat 502 is shown in FIG. 5. In a preferred embodiment of the kiosk system, user seat 502 is slideably-mounted to the left side of the kiosk system. User seat 502 is capable of sliding underneath the user-desk portion of the kiosk system so that a user in a wheelchair is able to put his or her wheelchair into position so as to use the kiosk system. As user seat 502 is slideable, it may be adjustable to several different positions at varying distances from the user desk portion 400 of the kiosk system. Alternatively, user seat 502 may be capable of continuous movement and placement at any practical distance from user desk portion 400: User seat 502 may additionally be equipped with a scale to accurately measure a user's weight, as described in Bluth et al., U.S. Pat. No. 6,403,897, which is incorporated herein by reference. In this situation, the scale of user seat 502 is communicatively coupled to the kiosk system so that either digital or analog weight data can be utilized to perform a health risk assessment for the user, can be incorporated into the user's PHR, can be transmitted to remotely located health care professionals, can be transmitted to various medical research databases in a non-personally-identifiable format, and/or can be stored locally and analyzed as appropriate. The precise weight-scale user seat apparatus and methods of use are described in Bluth et al., U.S. Pat. No. 6,403,897, which is incorporated herein by reference.

In addition to the various non-invasive health diagnostic input devices described above (question-and-answer input, visual input, verbal input, pulse oximeter input, blood glucose input, blood pressure and heart rate input, weight input, etc.), the kiosk system can also include invasive testing. For example, cholesterol testing, urine testing, and blood testing can be administered to a user by the kiosk system, with the help of licensed health care professionals (nurses, technicians, etc.). Such tests require a licensed professional to assist the user and to carrier out the test. Tools and supplies needed for these invasive tests can be stored on shelving units which may be built into the back side (not shown) of the kiosk system. A nurse or other licensed health care professional can administer the invasive test and then can input results, which may be referred to as invasive testing information, manually (via keyboard 403, via keyboard 303, or via touch-screen options). An invasive testing system used to analyze the invasively collected fluids can be connected to an additional port at the back of the kiosk system, or send its results over the network 108 to the kiosk system.

As previously noted, the kiosk system may also include several devices that can be described as output devices, such as a printer, as opposed to the various health diagnostic input devices. FIG. 5 includes a paper slot 506 in which paper output by a printer incorporated into the kiosk system is accessible by a user. The output paper may include printed answers to health assessment questions, results of various tests, a summary of information provided by the user, and many other types of data. FIG. 3 also illustrates a plan view of a triage version of the kiosk system that includes various output devices.

In FIG. 3, flatbed scanner 305 is located on the top of the kiosk system. Flatbed scanner 305 is communicatively coupled to the kiosk system, so that documents and information scanned in by a user is input into the system. Flatbed scanner 305 can be any type of commercially available scanner capable of receiving hard copy documents and converting them into electronically transferrable images or electronic documents. For example, a user may be able to scan in his or her health insurance card, identification or other documentation. The kiosk system software platform may be able to recognize certain information contained within the scanned-in documents—such as the user's social security number, for example—and fill in various forms automatically. For example, scanned-in medical records could be automatically incorporated into the user's PHR and/or be transmitted to a remotely located health care professional. Flatbed scanner 305 may be located on top of the kiosk, or may be embedded within a top portion of the kiosk system on a slideable tray, somewhat above where a seated user's head would normally be located, so that a user can slide flatbed scanner 305 out for use and then slide it in, and out of the way, after use. Alternatively, the scanner could be located on the front of the kiosk system, such as scanner 507 of FIG. 5. In such a situation, the scanner 507 might be placed on a tray that can slide out from the front of the kiosk system and be more readily accessible by users.

Printer 304 may also be located on top of the kiosk system, as is illustrated in FIG. 3. Alternatively, as previously noted, printer 304 may be embedded within an upper portion of the kiosk system, in such a way as to eject printed sheets of paper through a printer-eject slot 506 somewhat above where a seated user's head would normally be located. Printer 304 may be a standard commercial printer (laser, ink-jet, or other presently available technology) capable of printing either black-and-white documents, or full color documents. Alternatively in certain situations such as in triage, printer 304 may be a label-maker specifically designed to print-out situation-specific labels for use as user (patient) identifiers.

The kiosk system is designed to provide a user with a secure and private experience despite the fact that the kiosk system may be located in a very public space, such as a store, waiting room, office complex, etc. Privacy for the user is very important because a user may use the herein disclosed kiosk system to engage in personal medical discussions with a remotely located health care professional. Providing the user with a private setting will enable the user to feel completely comfortable discussing and listening to personal health care information. To further enhance the privacy of the setting, the kiosk system may include a privacy curtain 508, illustrated in FIG. 5, which can fully enclose the user during use of the kiosk system. Privacy curtain 508 slides along privacy track 510 to form a barrier between a user seated within the kiosk system and the surrounding room in which the kiosk system is located. Privacy curtain 508 may be designed to automatically move along privacy track 510 after a user sits down on the seat 502 at the kiosk system and engages the kiosk software platform. Alternatively, privacy curtain 508 may be designed to close after a user presses an appropriate button (not shown) on the user desk portion 400, or makes an appropriate selection within the software platform by touching an on-screen button or clicking of a computer mouse. Privacy curtain 508 would likewise open when the user has finished using the kiosk system, which may be indicated by selecting an appropriate physical button within the kiosk, selecting a software button, finishing a test or procedure, or getting up from the seat 502. The material of the privacy curtain 508 should be formed of any material that would help to reduce sound emanating from within the kiosk system during use so as to provide a user with a greater degree of privacy.

The kiosk system may also include a safety feature for disengaging in an emergency situation. For example, a hardware button may be included on the user desk portion 400 of the kiosk system that when pressed automatically releases a user's arm from blood pressure cuff test interface 504, and automatically opens privacy curtain 508, so that the user can quickly leave the kiosk system. FIG. 4 illustrates such a hardware release button 417 positioned on the right side of vertical panel 412 of the user desk portion 400 of the kiosk system. Alternatively, a software platform button or on-screen option may be available to the user that will quickly and automatically release the user's arm from blood pressure cuff test interface 504 and/or open privacy curtain 508. A similar hardware release button can be located on the back side of the kiosk system to allow a health care professional to quickly and automatically disengage blood pressure cuff test interface 504 and/or privacy curtain 508.

An additional privacy-enhancing feature of the herein disclosed kiosk system is the third-party display screen 512 illustrated in FIG. 5. Third-party display screen 512 is located on the side of the kiosk system, preferably near the top of the kiosk system so as to be easily viewable from some distance away. Third-party display screen 512 is a video monitor capable of displaying still images and full-motion video. Third-party display screen 512 may be a standard 15 to 17 inch monitor much like user display screen 406, or it may be different—smaller or bigger. The purpose of third-party display screen 512 is two-fold. First, to provide marketing and/or educational health-related information to persons in the vicinity of the kiosk system other than the immediate user seated within the kiosk system. For example, third-party display screen 512 may be connected to a DVD player and may play repeated loops of various health-related advertisements. Alternatively, third-party display screen 512 may display information on how to use the kiosk, or how to find a doctor in that particular geographic location. Third-party screen 512 may also be linked to the network 108 and therefore may be capable of streaming advertisements and/or informational feeds from any available Internet sources. A kiosk system may be equipped with several of these third-party display monitors, on various sides of the kiosk system, so that multiple messages may be displayed.

Third-party display screen 512 may include one or more speakers for emitting audio related to the video images displayed on screen. Audio related to the health information/advertisements establishes the second purpose of the third-party display screens, to provide a counter-point visual and audio stimulus that distracts anyone outside of the kiosk system from being able to hear or pay attention to any sound emanating from a user's use of the kiosk system. If someone other than the user is in close proximity to the kiosk, they would likely be distracted by images and sounds being generated, and therefore less likely to overhear a user consulting with a remotely located doctor.

While the present inventions have been illustrated and described herein in terms of a preferred embodiment and several alternatives associated with community-based health information and screening kiosk systems, it is to be understood that the various components of the combination and the combination itself can have a multitude of additional uses and applications. For example, the kiosk systems herein disclosed can easily be adapted to other settings or uses. Accordingly, the inventions should not be limited to just the particular descriptions and various drawing figures contained in this specification that merely illustrate one or more preferred embodiments and applications of the principles of the invention.

It should be apparent that the examples discussed above are only presented as examples. The various user-accessible menus, buttons, and interfaces are only one way to accomplish the more generally described systems, methods, apparatuses, and computer programs. For example, where certain features or user options are described as buttons, it may be apparent to those skilled in the art that the same function can be accomplished by using radio buttons, drop-down menus, or check-box-type options instead. All such available possibilities are intended to be covered by this specification.

Finally, it should be noted that where this specification describes a system for obtaining health information and screening, it is intended to cover related methods of utilizing the kiosk systems.

What is claimed is:

1. A kiosk system for providing prescription drugs comprising:
   a computer configured to present a health assessment questionnaire to the user and one or more input devices configured to receive user input for the health assessment questionnaire;
   a real-time communication system for communication with a health care professional, the real-time communication system comprising a camera, microphone, speaker, and video screen, the health care professional remote to the user;
   a privacy screen;
   a security mechanism comprising one or more of a thumbprint scanner, a signature pad, an access card, a pin, or verification of photo identification, the security mechanism operable to prevent unauthorized access to a personal health record accessible to the user and the health care professional;
   a prescription issuance mechanism configured to transmit, to the health care professional, a set of diagnostic information comprising audio and video information from the real-time communication system, the personal health record, and user input for the health assessment questionnaire, the prescription issuance mechanism further configured to receive a prescription issued by the health care professional based on the set of diagnostic information, the health care professional legally and ethically able to issue the prescription; and
   a drug dispenser configured to dispense a drug upon verification of the prescription, the drug dispenser further configured to dispense a prescribed amount of the drug in a consumer container.

2. The system of claim 1, wherein user input for the health assessment questionnaire is translated to English.

3. The system of claim 1, wherein the kiosk further comprises an audio speaker located on a side of the kiosk, the speaker configured to emit audio obstructing sound emanating from the user.

4. The system of claim 1, wherein the kiosk further comprises a video display located on a side of the kiosk, the video display providing marketing or educational information to persons situated outside the kiosk.

5. The system of claim 1, wherein the kiosk further comprises one or more inputs for diagnostic devices.

6. The system of claim 1, wherein the system further comprises a mechanism operable to receive invasive testing results at the kiosk and transmit the results of invasive testing to the health care professional.

* * * * *